United States Patent [19]
Borghi

[11] Patent Number: 5,314,461
[45] Date of Patent: May 24, 1994

[54] ACTIVELY ANCHORED ELECTRODE FOR ELECTRODE CATHETERS

[75] Inventor: Enzo Borghi, Budrio, Italy

[73] Assignee: X-Trode S.R.L., Bologna, Italy

[21] Appl. No.: 954,579

[22] Filed: Sep. 30, 1992

[30] Foreign Application Priority Data

Oct. 2, 1991 [IT] Italy .................. BO91A000351

[51] Int. Cl.⁵ .............................................. A61N 1/00
[52] U.S. Cl. .................................................. 607/127
[58] Field of Search ............... 128/783, 784, 785, 786, 128/642, 419 P, 419 D, 642; 607/115, 116, 119, 122, 127, 126

[56] References Cited

U.S. PATENT DOCUMENTS

| 4,233,992 | 11/1980 | Bisping | 128/785 |
| 4,282,885 | 8/1981 | Bisping | 128/785 |
| 4,566,467 | 1/1986 | DeHaan . | |

FOREIGN PATENT DOCUMENTS

| 0035959 | 9/1981 | European Pat. Off. . |
| 0191238 | 8/1986 | European Pat. Off. . |
| 0212955 | 3/1987 | European Pat. Off. . |
| 2949782 | 6/1981 | Fed. Rep. of Germany . |

*Primary Examiner*—Lee S. Cohen
*Assistant Examiner*—Jeffrey R. Jastrzab
*Attorney, Agent, or Firm*—Fay, Sharpe, Beall, Fagan, Minnich & McKee

[57] ABSTRACT

The electrode comprises an anchor point sandwiched firmly between a protective insulating sheath and an enlarged end portion of the selfsame sheath in such a way that the tip of the point projects from the distal end, together with a stimulation head disposed coaxially with the sheath and connected electrically to a spiral wound conductor; when the anchor point is corkscrewed into a cardiac muscle, a conductive spring positioned between the head and the conductor allows a measured retraction of the head back into the sheath, with the result that the head is maintained constantly in contact with the surface of the cardiac muscle independently of the penetrating movement of the point.

6 Claims, 2 Drawing Sheets

ACTIVELY ANCHORED ELECTRODE FOR ELECTRODE CATHETERS

BACKGROUND OF THE INVENTION

The present invention relates to an actively anchored electrode for electrode catheters. Conventional electrode catheters as used currently with cardiac pacemakers, whether mono- bi- or tri- polar, are anchored by way of a distal electrode consisting substantially in a head or point of conductive material that is hooked into the cardiac muscle and associated directly (via a connection made internally of a protective insulating sheath) to a spiral wound conductive wire returning to one of the pacemaker terminals.

During implantation of the catheter, the surgeon uses a special tool operated from the remote end of the spiral wound conductor to corkscrew the point into the cardiac muscle of the patient, where it remains permanently anchored.

The principal drawback betrayed by these implanted elements stems in effect from the very embodiment of the electrode catheter, whereby the point, being connected directly and electrically to the spiral wound wire, also functions as a cardiac sensing and stimulation terminal; the surface area of such an electrode is therefore of generous proportions, so that the concentration of the stimulation current flowing through the lesion produced in the cardiac muscle by penetration of the point gives rise to a negative secondary phenomenon in the electrical activity of the heart, referred to in technical jargon as a "lesion wave".

Accordingly, the object of the present invention is to overcome the drawback in question by providing an electrode capable on the one hand of allowing a secure penetration and anchorage in muscle tissue, and on the other, of producing electrical contact by way of a conductive surface that is proportioned to the requirements of stimulation, devoid of any traumatizing effect and with a greater stimulation sensitivity, the combined effect of which being to eliminate the "lesion wave".

SUMMARY OF THE INVENTION

The stated object is comprehensively realized in an actively anchored electrode according to the present invention.

The electrode disclosed comprises a protective insulating tubular sheath, at least one spiral wound stimulation signal conductor accommodated internally of the sheath, and an anchor terminal or point positioned at and projecting from the distal end of the catheter, rotatable through the agency of control means in such a way as to penetrate and anchor in a cardiac muscle, which is connected stably to the sheath in a position coinciding with an enlarged end portion of the sheath and isolated electrically from the spiral wound conductor.

To advantage, the electrode further comprises a stimulation head disposed coaxially with the sheath and connected to the spiral wound conductor, which in a non-operative configuration of the catheter is at least partly encircled by the anchor point and disposed with its exposed surface in alignment at least with the tip of the point, and a conductive spring interposed between the stimulation head and the spiral wound conductor, of which the purpose is to allow a measured retraction of the head into the sheath when the anchor point is made to penetrate the cardiac muscle, such that the contact induced between the head and the surface of the cardiac muscle can be maintained constant independently of the penetrating movement of the point.

BRIEF DESCRIPTION OF THE DRAWINGS

The invention will now be described in detail, by way of example, with the aid of the accompanying drawings, in which.

DESCRIPTION OF THE PREFERRED EMBODIMENTS

Figure 1:
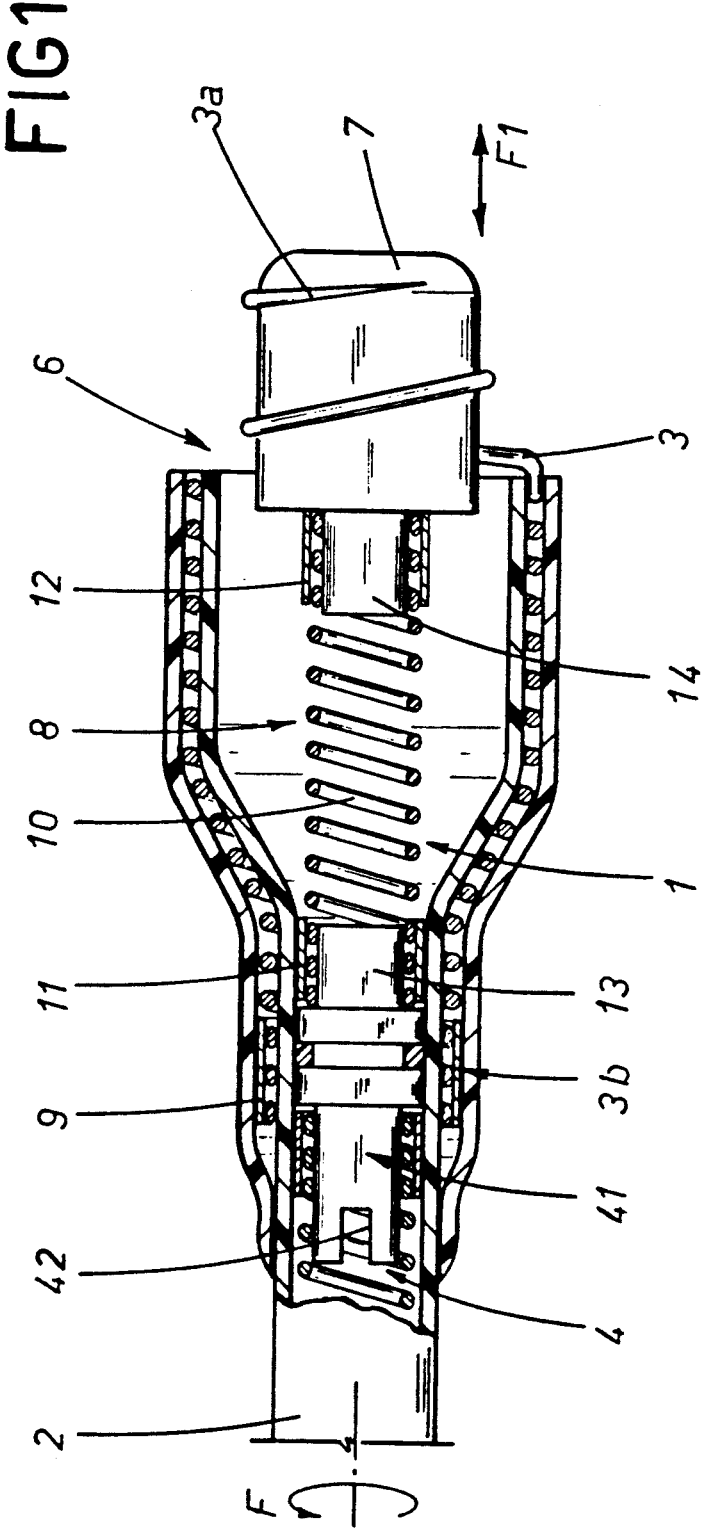
FIG. 1 is the side elevation of an anchor electrode according to the invention, seen in a non-operative configuration and with certain parts illustrated in section.

With reference to the accompanying drawings, the actively anchored electrode disclosed forms part of an indwelling electrode catheter comprising one or more spiral wound stimulation signal conductors 1; the number of conductors will depend naturally upon the type of electrode catheter in question (mono - or bi- or tri-polar), though the conductor with which the disclosure is especially concerned is that denoted 1, extending to the distal extremity of the catheter.

The spiral wound conductor is clad in a protective tubular sheath 2 of insulating material and affords a metallic anchor terminal, or point 3, located at the free end of the catheter, which can be rotated through the agency of control means 4 consisting in a spindle 41, capable of rotation about its own axis and affording a slot 42 in the face offered to the conductor 1; inserting a surgical screwdriver into the slot and turning the spindle, the point 3 can be made to penetrate into the cardiac muscle 5 and thus anchored.

More exactly, the anchor point 3 of the electrode according to the invention forms part of a spiral wound element sandwiched (see FIG. 1) between the tubular sheath 2 and an enlarged terminal portion 6 of the sheath, likewise of insulating material, with the tip 3a lying substantially beyond the compass of the sheath 2.

The anchor point 3 is rigidly associated with the control means 4 by way of a ring 9 crimped over the innermost end 3b of the sandwiched spiral element in a position coinciding with that occupied by the control means 4. In a non-operative position, the active or exposed coils of the point 3 encircle a stimulation element or head 7 disposed coaxially to the tubular sheath 2 and connected to the spiral wound conductor 1; similarly, in the non-operative position, the active surface of the stimulation head 7 is positioned substantially in alignment with the tip 3a of the anchor point 3.

In the example illustrated, the stimulation head 7 consists in a pin of cylindrical shape which might be embodied in a variety of materials, typically platinum-/iridium, carbon, titanium etc.

The connection between the stimulation head 7 and the spiral wound conductor 1 is achieved utilizing conductive elastic means 8 interposed between the two components; such means 8 consist effectively in a coil spring 10 of conductive material, positioned between the control spindle 41 and the stimulation head 7, of which the ends are secured by means of corresponding rings 11 and 12 crimped onto relative pins 13 and 14 associated with the spindle 41 and the head 7 respectively, over which the two ends of the spring 10 are coaxially seated.

The function of the coil spring 10 is to allow a measured retraction of the stimulation head 7 back into the sheath 2 as the point 3 screws into the cardiac muscle 5, thereby ensuring that the contact induced between the head and the surface of the muscle is maintained constant independently of the penetrating movement of the point 3.

An electrode according to the present invention is positioned and anchored in the following manner: locating the point 3 against the cardiac muscle 5, the surgeon, using a special flexible screwdriver inserted through the tubular sheath 2 and located in the slot of the spindle 41, applies pressure and rotation (see arrows F and F1); given the position of the spindle 41 between the conductor 1 and the spring 10, the effect of such a maneuver is to carry both the head 7 and the point 3 forward.

Figure 2:
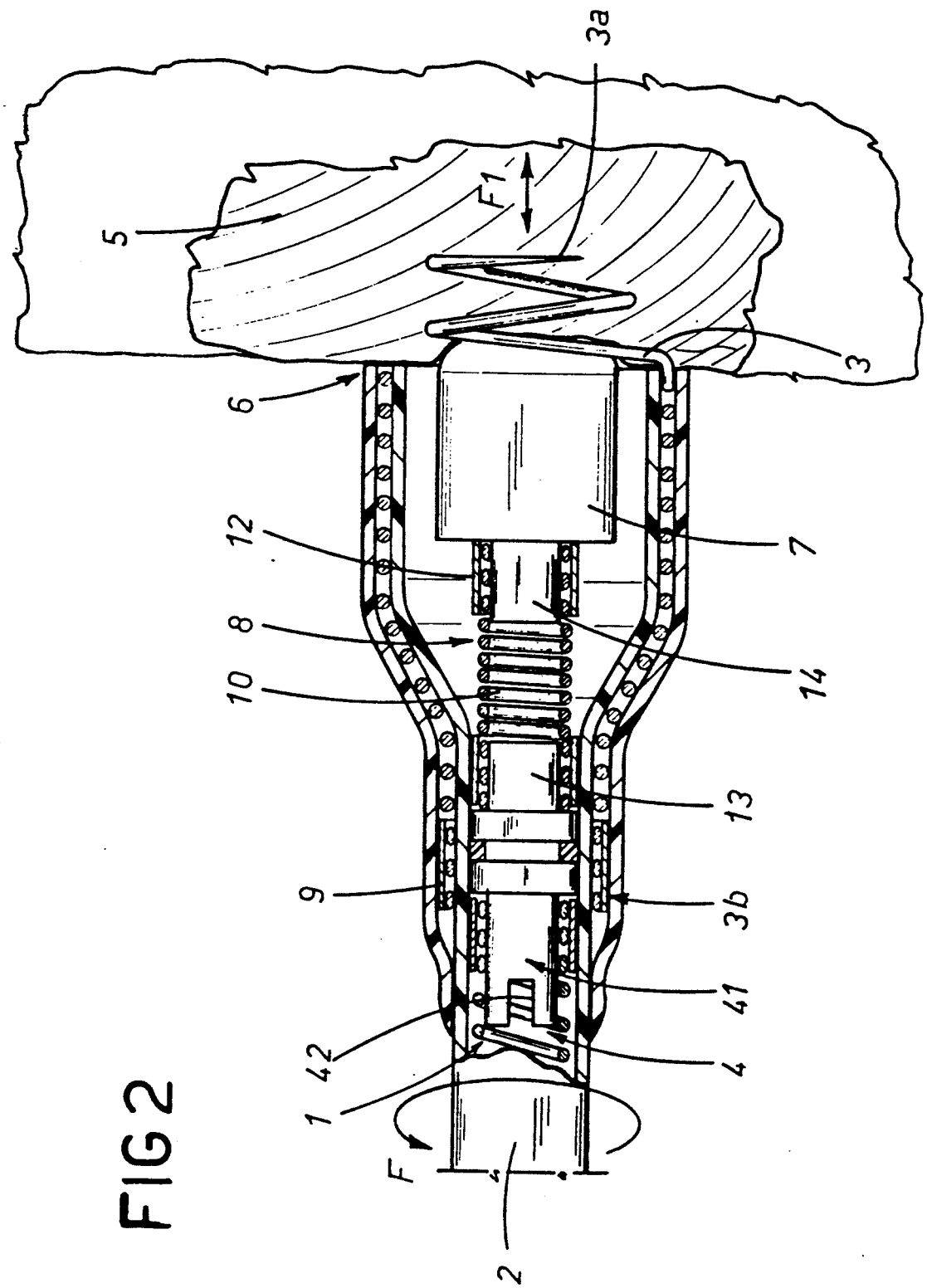
FIG. 2 is a further side elevation illustrating the anchor electrode of FIG. 1, seen in an operative configuration and with certain parts in section.

As the tip 3a enters into contact with the cardiac muscle 5 and begins to penetrate, the stimulation head 7 also engages the surface of the muscle, and through the agency of the spring 10 is held in this same position as the active coils of the point 3 and the corresponding extremity of the sheath 2 are carried forward until the sheath also enters into contact with the muscle (as in FIG. 2).

Thus, an electrode embodied in the manner described above ensures efficient anchorage of the electrode catheter as a whole, together with improved levels of sensitivity in monitoring and stimulating the cardiac muscle, achieved by virtue of the type of head 7 and the materials used in its construction.

More important still is the fact that the anchor point and the spiral wound conductor are isolated one from the other: thus, with the electrically conductive surface area offered by the electrode to the cardiac muscle reduced in size, the lesion wave returned by the muscle (detectable with appropriate instruments) is almost completely eliminated.

What is claimed is:

1. An actively anchored electrode catheter comprising:

a protective insulating tubular sheath having an enlarged end portion;

at least one spiral wound stimulation signal conductor accommodated internally of the sheath;

a spiraled anchor point ending in a tip, positioned at and projecting from a distal end of the tubular sheath a rotation control means, connected stably to the protective tubular sheath in a position coinciding with the enlarged end portion of the sheath and isolated electrically from the spiral wound conductor, for rotating the spiraled anchor point causing the spiraled anchor point to penetrate a cardiac muscle thereby anchoring the electrode catheter;

a stimulation head disposed coaxially with the sheath and connected to the spiral wound conductor, at least partly encircled by the spiraled anchor point, of which an exposed surface is disposed in alignment at least with the tip of the point in a non-operative configuration of the catheter;

conductive elastic means interposed between the stimulation head and the spiral wound conductor for allowing a measured retraction of the head into the sheath as the spiraled anchor point is made to penetrate the cardiac muscle, in such a way that the contact induced between the head and the surface of the cardiac muscle can be maintained constant independently of the penetrating movement of the point.

2. An electrode as in claim 1, wherein the point forms part of a spiral wound element lodged between an end of the protective tubular sheath and the enlarged end portion of the sheath, and is operatively connected to the rotation control means disposed coaxially between the spiral wound conductor and the elastic means with a ring crimped to an innermost end of the element in such a way that the innermost end remains secured to the tubular sheath in a position coinciding with the rotation control means.

3. An electrode as in claim 1, wherein elastic means consists of a conventional spring of conductive material interposed between the rotation control means and the stimulation head, the stimulation head having a pin extending coaxially through a first end of the conventional spring, the rotation control means having a pin extending through a second end of the conventional spring, said ends being attached to their respective pins by corresponding crimped rings.

4. An electrode as in claim 1, wherein the stimulation head consists of a cylindrical pin fashioned from platinum-iridium.

5. An electrode as in claim 1, wherein the stimulation head consists of a cylindrical pin fashioned from titanium.

6. An electrode as in claim 1, wherein the stimulation head consists of a cylindrical pin fashioned from carbon.

* * * * *